United States Patent
Manassen et al.

(10) Patent No.: US 9,581,430 B2
(45) Date of Patent: Feb. 28, 2017

(54) PHASE CHARACTERIZATION OF TARGETS

(71) Applicant: KLA-Tencor Corporation, Milpitas, CA (US)

(72) Inventors: Amnon Manassen, Haifa (IL); Ohad Bachar, Timrat (IL); Daria Negri, Nesher (IL); Boris Golovanevsky, Haifa (IL); Barak Bringoltz, Rishon Le Tzion (IL); Daniel Kandel, Aseret (IL); Yoel Feler, Haifa (IL); Noam Sapiens, Bat Yam (IL); Paykin Irina, Haifa (IL); Alexander Svizher, Haifa (IL); Meir Aloni, Herzliya (IL); Guy Ben Dov, Haifa (IL); Hadar Shalmoni, Beit Oved (IL); Vladimir Levinski, Migdal HaEmek (IL)

(73) Assignee: KLA-Tencor Corporation, Milpitas, CA (US)

(*) Notice: Subject to any disclaimer, the term of this patent is extended or adjusted under 35 U.S.C. 154(b) by 66 days.

(21) Appl. No.: 14/057,827

(22) Filed: Oct. 18, 2013

(65) Prior Publication Data
US 2014/0111791 A1  Apr. 24, 2014

Related U.S. Application Data

(66) Substitute for application No. 61/745,981, filed on Dec. 26, 2012.
(Continued)

(51) Int. Cl.
G01B 9/02 (2006.01)
G01N 21/45 (2006.01)

(52) U.S. Cl.
CPC ....... *G01B 9/0209* (2013.01); *G01B 9/02027* (2013.01); *G01B 9/02043* (2013.01); *G01B 9/02087* (2013.01); *G01N 21/45* (2013.01)

(58) Field of Classification Search
CPC ............ G01B 9/02027; G01B 9/02043; G01B 9/0209; G01N 21/45
See application file for complete search history.

(56) References Cited

U.S. PATENT DOCUMENTS 6,710,876 B1  3/2004 Nikoonahad et al.
2003/0048532 A1*  3/2003 Lindner et al. ............... 359/511
(Continued)

OTHER PUBLICATIONS

Lago, E. Lopez et al. "Amplitude and phase characterizatoin by diffracted beam interferometry: blind dbi". Journal of Physics Conference Series 274(1):012029, Feb. 2011.*
(Continued)

*Primary Examiner* — Michael A Lyons
(74) *Attorney, Agent, or Firm* — Simpson & Simpson, PLLC (57) ABSTRACT

Systems and methods are provided which derive target characteristics from interferometry images taken at multiple phase differences between target beams and reference beams yielding the interferometry images. The illumination of the target and the reference has a coherence length of less than 30 microns to enable scanning the phase through the coherence length of the illumination. The interferometry images are taken at the pupil plane and/or in the field plane to combine angular and spectroscopic scatterometry data that characterize and correct target topography and enhance the performance of metrology systems.

12 Claims, 8 Drawing Sheets

Related U.S. Application Data

(60) Provisional application No. 61/716,137, filed on Oct. 19, 2012.

(56) References Cited

U.S. PATENT DOCUMENTS

| | | | |
|---|---|---|---|
| 2009/0262362 A1* | 10/2009 | de Groot et al. | 356/508 |
| 2012/0229814 A1* | 9/2012 | Freimann et al. | 356/512 |
| 2013/0035888 A1 | 2/2013 | Kandel et al. | |

OTHER PUBLICATIONS

U.S. Appl. No. 61/664,477, filed Jun. 26, 2012.

\* cited by examiner

PHASE CHARACTERIZATION OF TARGETS

CROSS-REFERENCE TO RELATED APPLICATIONS

This application claims the benefit under 35 U.S.C. §119 (e) of U.S. Provisional Patent Application No. 61/716,137, filed Oct. 19, 2012 and U.S. Provisional Patent Application No. 61/745,981, filed Dec. 26, 2012, which applications are incorporated herein by reference.

BACKGROUND OF THE INVENTION

1. Technical Field

The present invention relates to the field of metrology, and more particularly, to target characterization.

The present invention relates to the field of metrology, and more particularly, to target characterization.

2. Discussion of Related Art

Target imperfections are becoming a limiting factor in wafer metrology, as overlay scatterometry methods become evermore accurate while target inspection method either lag behind or depend on extensive modeling or slow measurement procedures.

SUMMARY OF THE INVENTION

One aspect of the present invention provides a system comprising: an illumination source arranged to produce electromagnetic radiation having a coherence length of less than 30 microns, a reference optical element, as well as a phase controlled interferometer arranged to receive the radiation from the illumination source, split the radiation between a target and the reference optical element, wherein the interferometer is arranged to controllably introduce a phase between radiation directed to the target and to the reference optical element, and generate, from reflected radiation from the target and from the reference optical element, an interference beam. The system further comprises an imaging unit arranged to receive the interference beam and generate a plurality of interferometry images corresponding to different introduced phases at at least one of a pupil plane and a field plane, and an analysis unit arranged to derive from the interferometry images at least one target characteristic.

These, additional, and/or other aspects and/or advantages of the present invention are set forth in the detailed description which follows; possibly inferable from the detailed description; and/or learnable by practice of the present invention.

BRIEF DESCRIPTION OF THE DRAWINGS

For a better understanding of embodiments of the invention and to show how the same may be carried into effect, reference will now be made, purely by way of example, to the accompanying drawings in which like numerals designate corresponding elements or sections throughout.

In the accompanying drawings.

DETAILED DESCRIPTION OF THE INVENTION

Prior to the detailed description being set forth, it may be helpful to set forth definitions of certain terms that will be used hereinafter.

The term "field plane" as used in this application refers to an optical plane at which an imaged target is focused.

The term "pupil plane" as used in this application refers to an optical plane at which an illumination source is focused.

The term "optical properties" as used in this application refers to any material property as well as any property of a material layer that effect light propagation therethrough, for example the refractive index of the material, the thickness of the layer, birefringence, internal structure, material composition etc.

The terms "angular (angle dependent) scatterometry" and "spectral (wavelength dependent) scatterometry" as used in this application refer to scatterometry methods which analyze the angular distribution and the spectral distribution of reflected radiation, respectively.

The terms "spectral signature" and "spectrogram" as used in this application refer to the dependency of the intensity of measured radiation on its wavelength and to any representation of this dependency. The spectral signature may be measured for a whole image, for a region in the image, for a single pixel or for a part of a single pixel.

The term "phase control" as used in this application refers to the adjustment of a difference in the optical path between two beams, which may be achieved by any means such as changing a path length, changing respective lengths of different materials in the path or directing light along different paths.

The term "phase map" as used in this application refers to a dependency of an image parameter (such as but not limited to intensity and spectral signature relating to the whole image, image parts of pixels) on an introduced phase difference or a range of introduced phase differences.

The term "interferometer" as used in this application refers to any device which generates an interferometry image of at least two beams, typically but not limited to beams from a target and from a reference with a controlled difference in optical path between them.

The term "coherence length" as used in this application refers to a distance along which a radiation may be considered coherent according to a specified criterion. In particular, the coherence length of a given radiation determines the extent to which a phase difference between two parts of the radiation results in a detectable change in an interferometry image of these parts. A short coherence length leaves less room for phase manipulation than a longer coherence length. The range of coherence lengths referred to in the present application may range from less than a single micron to tens of microns, and is not limited to specific examples that are given in the text.

The term "broadband" as used in this application refers to a range of wavelengths which is included in a specific radiation. This range may be continuous or discrete, and may be composed of several distinct bands (or sub-ranges). As a non-limiting generalization, the width of the wavelength range is reciprocal to the coherence length of the radiation as may thus be used to adjust the coherence length of the radiation.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Before at least one embodiment of the invention is explained in detail, it is to be understood that the invention is not limited in its application to the details of construction and the arrangement of the components set forth in the following description or illustrated in the drawings. The invention is applicable to other embodiments or of being practiced or carried out in various ways. Also, it is to be understood that the phraseology and terminology employed herein is for the purpose of description and should not be regarded as limiting.

Figure 1A:
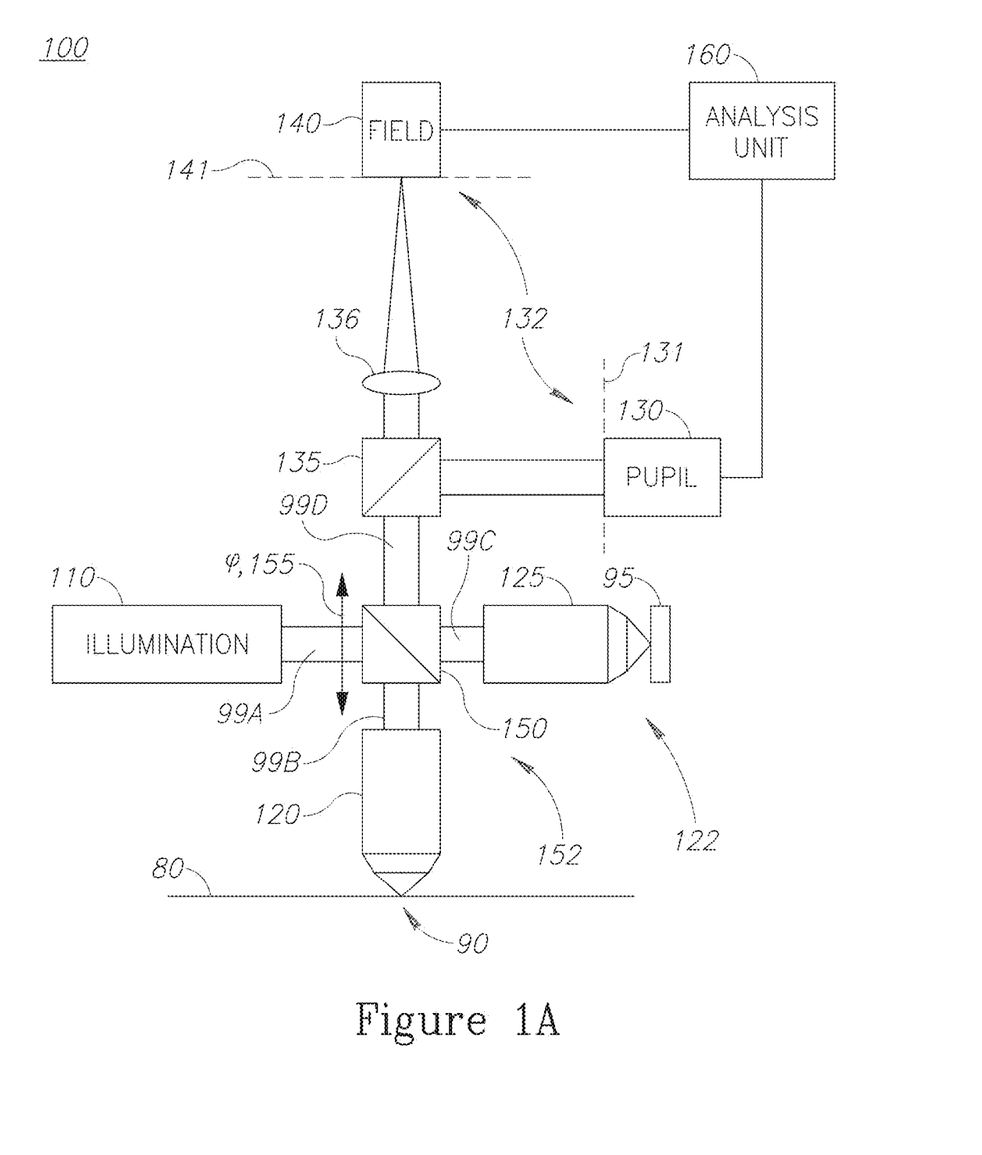
FIGS. 1A and 1B are high level schematic block diagrams of a system, according to some embodiments of the invention.
Figure 1B:
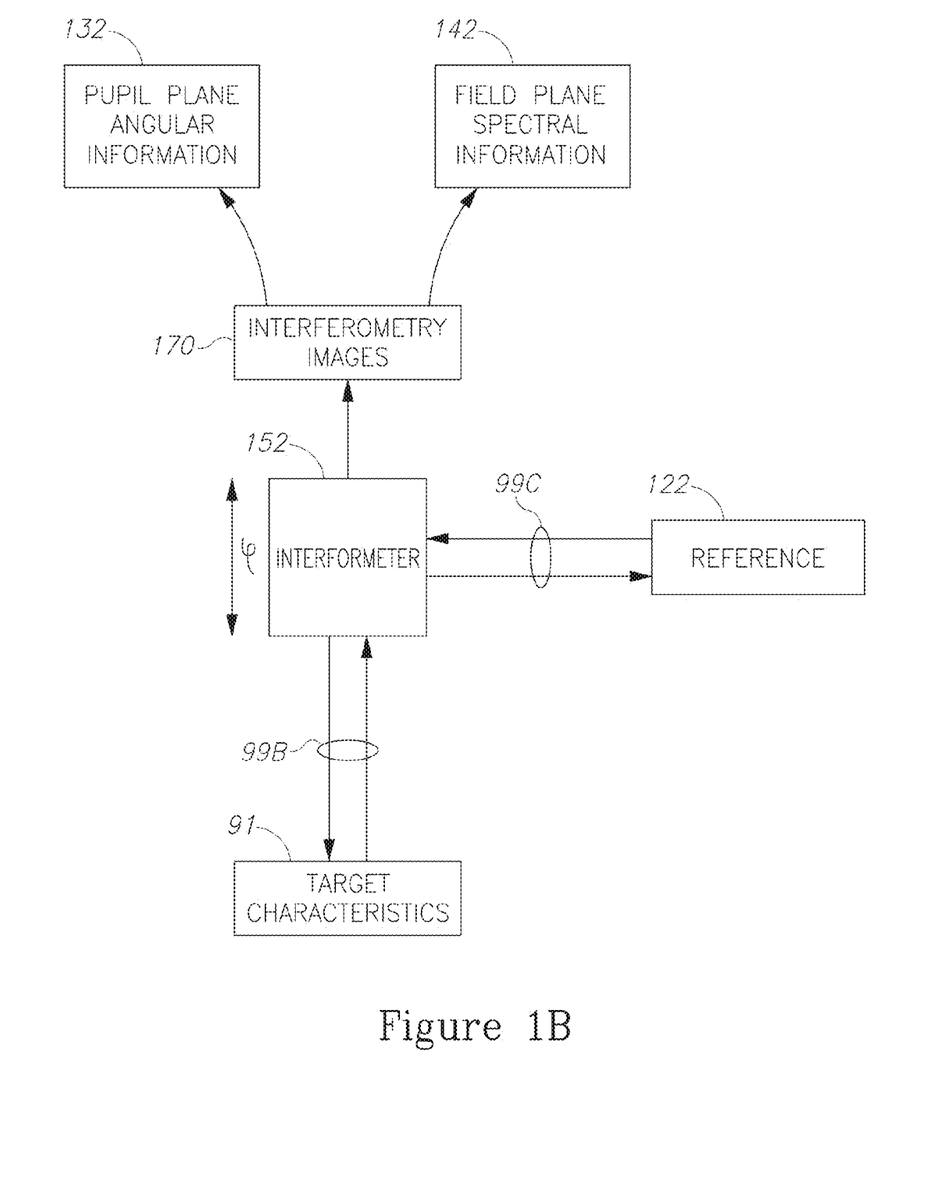

FIGS. 1A and 1B are high level schematic block diagrams of a system 100 according to some embodiments of the invention. System 100 comprises an illumination source 110 arranged to produce broadband electromagnetic radiation 99A, e.g., one having a coherence length of less than 30 microns. In certain embodiments, the illumination may comprise one or more radiation bands in a wide range of the spectrum, e.g. from infrared to deep ultraviolet (e.g., at least one band within a wavelength range of 170-900 nm). In an example, the illumination may be with white light. The coherence length of the illumination may range between sub-microns and tens of microns. The relatively short coherence length of the illumination allows effective phase scanning with high sensitivity to target characteristics, as explained below.

System 100 further comprises a reference optical element 122 and a phase controlled interferometer 152 arranged to receive radiation 99A from illumination source 110, split radiation 99A between a target 90 on a wafer 80 (99B) and reference optical element 122 (99C). Interferometer 152 is further arranged to controllably introduce a phase (phi-$\phi$) between radiation directed to target 90 (99B) and to reference optical element 122 (99C) and to generate, from reflected radiation from target 90 (99B) and from reference optical element 122 (99C), an interference beam 99D. System 100 further comprises an imaging unit 132 (e.g., a pupil detector 130 or a field detector 140) arranged to receive interference beam 99D and generate a plurality of interferometry images 170 corresponding to different introduced phases ($\phi$) at at least one of a pupil plane (131) and a field plane (141), and an analysis unit 160 arranged to derive from interferometry images 170 at least one target characteristic 91.

For example, interferometer 152 may comprise a mechanically movable beam splitter 155 and reference element 122 may comprise a mirror 95 (e.g., for obtaining only pupil images) or a mirror 95 with reference objective 125, such as an objective identical to a target objective 120, to ensure that target beam 99B and reference beam 99C traverse identical optical paths (and creating a twin reference beam for each target beam). System 100 may be arranged in a way that the only difference in the optical paths of target beam 99B and reference beam 99C is the introduced phase $\phi$. In certain embodiments, phase controlled interferometer 152 may be arranged to scan the phase $\phi$ through the coherence length of the illumination radiation. In certain embodiments, the phase $\phi$ may be introduced by shifting reference objective 125 (and/or shifting mirror 95) along its optical axis instead or in addition to moving interferometer 152.

For example, interferometry images of target 90 may be grabbed for varying optical path differences (OPD) between the measurement and reference arms. In doing so, the reference phase scans vary the image contrast grabbed by the camera. The contrast can potentially vary between zero and full contrast (corresponding e.g., to 250 grey levels) as the phase difference between measurement and reference arms varies 180° which amounts to half wavelength OPD (e.g., ca. 250 nm). Using cameras 130 and/or 140 with camera sensitivity of 1 grey level thus enables detecting down to ca. 1 nm deviations of target regularity. This accuracy may improve current target related inaccuracies (>5 nm level) by up to an order of magnitude and bring them to the order of magnitude of overlay tool accuracies (<1 nm level). Using phase characterization allows calibrating the metrology tool to overcome target related inaccuracies and mitigate internal deficiencies originating from spectral dependencies. Additional information can be achieved about the target by analyzing the interferogram per pixel and thus inferring the reflected spectrum (see below).

Interferometry images 170 may be measured by a pupil camera 130 and/or by a field camera 140, after being split by a beam splitter 135 (with a lens 136 that focuses interferometry images 170 onto field plane 141). As pupil plane interferometry images depict angular information from target 90 and field plane interferometry images depict spectral information from target 90, system 100 de-correlates these two types of information and allows extracting data from interferometry images 170 that is otherwise, without using phase difference interferometry, not extractable.

In certain embodiments, at least one target characteristic 91 may comprises any of the following, as explained in detail below: target topography, target side wall angles (SWA), a target asymmetry merit, film thickness, film optical parameters and exposed layer quality before layer development. In certain embodiments, analysis unit 160 may be arranged to carry out, according to derived target characteristic 91, any one of the following, as explained in detail below: detect edges of unresolved features, correct target measurements and enhance metrology measurements.

Figure 2:
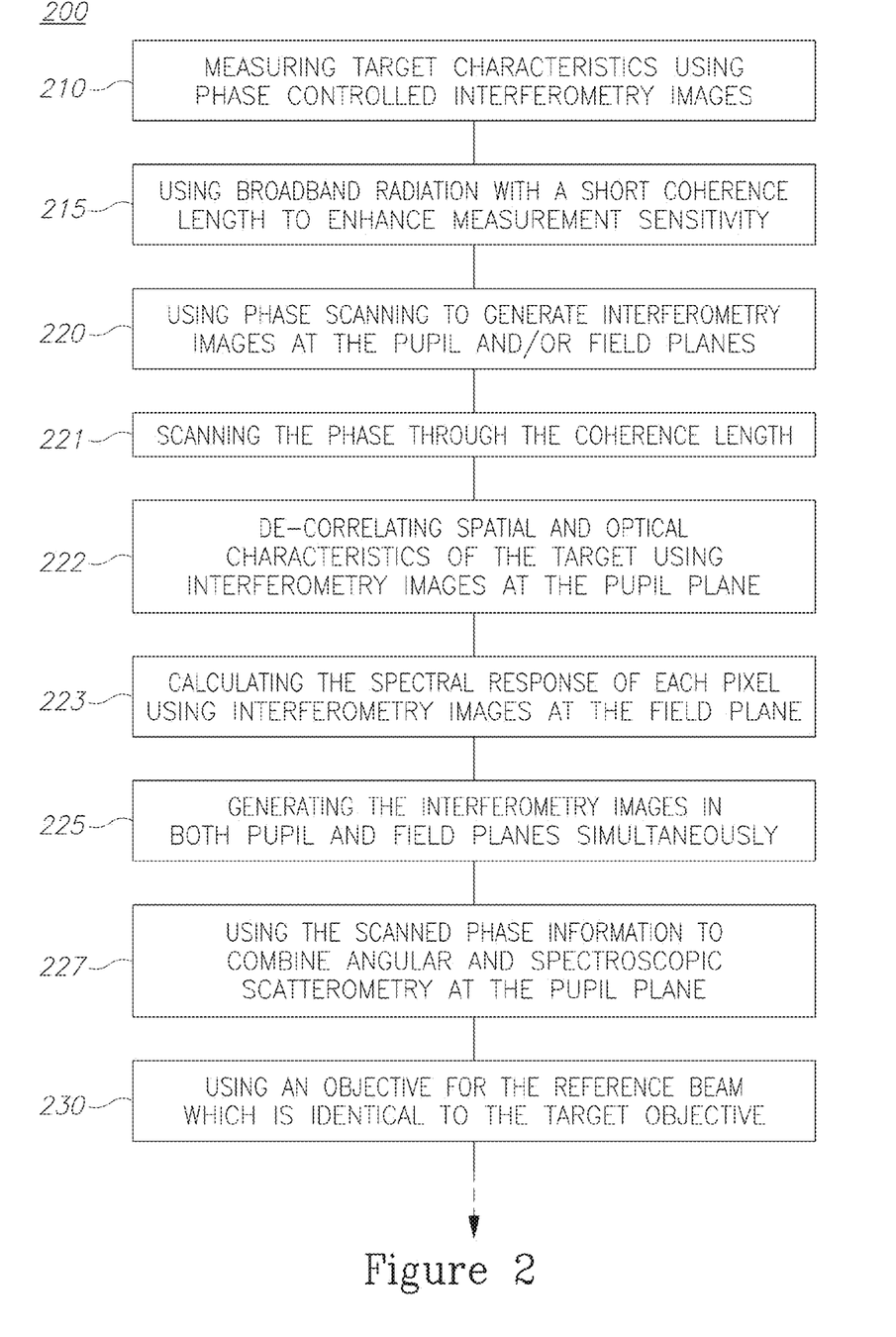
FIG. 2 is a high level schematic block diagram of a method, according to some embodiments of the invention.

FIG. 2 is a high level schematic block diagram of a method 200 according to some embodiments of the invention. Method 200 may comprise any of the following stages.

Method 200 comprises deriving at least one target characteristic (stages 210, 260) from a plurality of interferometry images taken at a respective plurality of phase differences between target beams and reference beams yielding the interferometry images (stage 250), wherein an illumination of the target and the reference has a coherence length of less than 30 microns (stage 215) and wherein the interferometry images are taken at at least one of a pupil and a field plane (stage 220).

In certain embodiments, method 200 comprises grabbing interferometry images of targets with controlled phase delays (stage 250), analyzing the grabbed images to identify target characteristics (stage 260) and analyzing the targets from the target characteristics (stage 270). In certain embodiments, method 200 comprises using broadband radiation with a short coherence length to enhance measurement sensitivity (stage 215) and using phase scanning to generate interferometry images at the pupil and/or field planes (stage 220). In certain embodiments, method 200 comprises measuring target characteristics using phase scanning (stage 210) and using the scanned phase information to combine angular and spectroscopic scatterometry at the pupil plane (stage 227), thereby de-correlating spatial and optical characteristics of the target using interferometry images at the pupil plane (stage 222). Method 200 may comprise controlling reference phase delays (stage 240) to optimize the derivation of target characteristics.

In certain embodiments, method 200 comprises scanning the phase through the coherence length (stage 221) to extract all available phase information from the illumination beam. Reconstructing the entire interferogram, namely taking images with reference phases that span the entire coherence lengths facilitates Fourier transforming each pixel through its phase values and thus retrieving the spectral response per point. Such scanning provides target asymmetry information as well as metrology data (see below). In certain embodiments, the coherence length of the broadband illumination may be selected according to parameters of the required extent of phase scanning. In certain embodiments, method 200 comprises maintaining the same optical path for the target and reference beams (stage 235) to minimize artifacts in the interferometry images, for example by sing an objective for the reference beam which is identical to the target objective (stage 230).

Target Imperfection Characterization and Correction

At field plane 141, image pixels correspond to areas on target 90, from which a spectral signature is derived by the phase scanning. These measurements allow deriving target quality parameters and correct metrology measurements according to derived target characteristics 91. Using phase characterization to derive pixel spectral signatures is advantageous over spectral methods as it solves the problem of uncontrolled phase shifts due to target topography, which create imaging errors (e.g., reflection from a different layer). Using phase characterization allows identifying two points of target 90 as being in the same layer by correcting the phase according to spectral difference (phase error resulting from topography). Moreover, spectrometric data related to optical parameters of target 90 (e.g., the refraction index) may be combined with imaging data (e.g., target topography) to enhance the target monitoring data.

In certain embodiments, imaging unit 152 may be arranged to generate interferometry images 170 at field plane 141 and the analysis unit is arranged to characterize and correct target imperfections identified from the phase controlled interferometry images.

In certain embodiments, imaging unit 152 may change the segmentation of target 90 with respect to the pixels of imaging unit 132 (e.g., field camera 140) to detect spectral signatures of segment edges within pixels. In certain embodiments, segmentation may be carried out at multiple levels.

In certain embodiments, method 200 comprises calculating a spectral response of each pixel using interferometry images at a field plane (stage 223). For example, method 200 may comprise obtaining a response of each pixel at all wavelengths of the broadband radiation (stage 265) and using a Fourier transform of the grabbed interferometry images at the field plane through the phase values to calculate the spectral response of each pixel (stage 266).

In certain embodiments, method 200 comprises deriving target topography (stage 262) from generated wavelength specific phase maps (stage 261). In certain embodiments, method 200 comprises interpolating target topography from the phase maps (stage 263). In certain embodiments, method 200 comprises characterizing and correcting target imperfections as derived from the target characteristics (stage 275). Imaging unit 132 and analysis unit 160 may be arranged to carry out these method stages. Advantageously, in certain embodiments, method 200 and system 100 enable accurate topographic characterization of the entire target and without modifying the spectrum of illumination.

Measuring Unresolved Features

In certain embodiments, method 200 comprises detecting edges of unresolved features from the spectral signature (stage 310), for example from detected spectral changes at different phase differences in unresolved features (stage 312). Method 200 may comprise localizing unresolved features from the detected edges (stage 314) and focusing the spectral signature on edges to measure unresolved features (stage 316).

In certain embodiments, method 200 may comprise applying different image segmentations to identify edges of target elements within pixels (stage 276) and applying image segmentation at multiple levels (stage 277) to maximize or optimize the obtained information regarding the unresolved features.

In certain embodiments, the illumination bandwidth and wavelengths may be controlled to enhance the edge detection of unresolved features, thus making phase scanning more efficient.

Advantageously, phase scanning may be more efficient than spectral scanning in detecting unresolved features due to its added sensitivity to phase information, over and above its sensitivity to spectral information.

Monitoring Target Asymmetries, Wafer Induced Shift (WIS) and Side Wall Angle (SWA) Variation In certain embodiments, method 200 comprises estimating wafer induced shift (WIS) from the analyzed interferometry images (stage 274). In the field of optical metrology and in particular overlay metrology, increasing attention is given to targets quality as a measurement error source. As overlay is a symmetry measurement, any target imperfection that translates into an asymmetry signal in the metrology tool is a source for measurement inaccuracy. This error is termed Wafer Induced Shift (WIS). In past overlay tool generations the tool induced shift (TIS), namely the measurement error originating from the tool, was of the order of or larger than WIS. However in the new overlay tool generations TIS and TIS variability values are often <1 nm while many indications exist that the WIS values many times surpass 5 nm. This level of tool performance enables the use of the tool for characterization of WIS down to values of TIS where the tool itself may again become the main error source. Advantageously, the ability to reliably characterize WIS allows to remove its contribution from the measurement and thus to improve accuracy. Examples for such a removal process are measurement parameters selection in which WIS is small or characterizing the proportionality factor between WIS and overlay and thus subtracting its contribution from the overlay result.

In certain embodiments, method 200 comprises evaluating an asymmetry merit from the analyzed interferometry images (stage 272). For example, the asymmetry merit may be derived from penetration depth variation of different wavelengths into the target and phenomenological calibration of topographic asymmetry target errors. In certain embodiments, the asymmetry merits may be similar to or derived from the ones disclosed in U.S. Patent Document No. 2013/0035888, incorporated hereby by reference in its entirety. Grabbing interferometry images of targets with controllable reference phase delays followed by image analysis enable surfaces variations measurement to nanometer accuracies and can be used to characterize target asymmetries using different methods. For example the target uniformity in different reference phase values can be evaluated or the reference phase variation of spectral based asymmetry merits can be characterized. The use of such phase based values may resolve all contributions to target asymmetries by using both spectral and angular information.

In certain embodiments, method 200 comprises analyzing target side wall angles (SWA) from the derived target topography (stage 264). SWA is of particular interest as it is related to scanner focus direction when measuring photoresist targets. The sectioning capability of the phase dependent images may be used to reveal SWA variation and thus monitoring scanner focus repeatability.

Figure 3A:
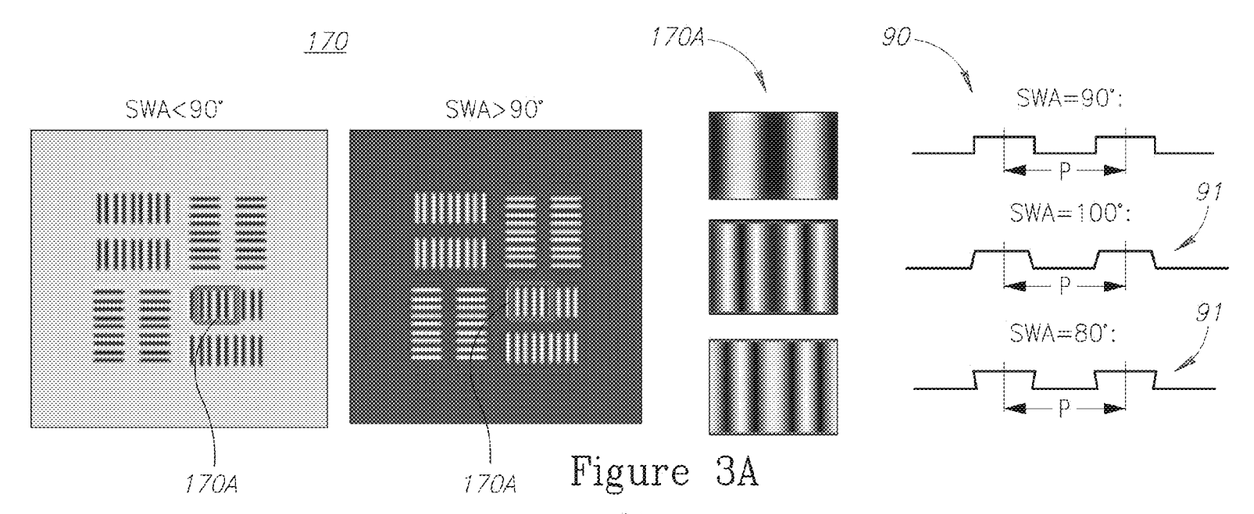
FIGS. 3A and 3B schematically illustrate target asymmetries which the phase characterization measures and monitors, according to some embodiments of the invention.
Figure 3B:
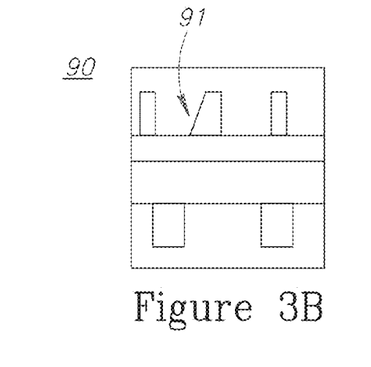

FIGS. 3A and 3B schematically illustrate target asymmetries which the phase characterization measures and monitors, according to some embodiments of the invention. FIG. 3A illustrates simulated targets having a SWA of 90°, 100° and 80° and respective expected interferometry images 170 with enlarged details 170A that indicate the difference in the respective SWA as target characteristic 91 (target pitch is marked by p). FIG. 3B illustrates a target asymmetry 91 which can similarly be detected and monitored using phase characterization of target 90.

Film Monitoring and Monitoring of Film Development

At pupil plane 131, image pixels correspond to angles of reflection and diffraction from target 90, from which a spectral signature is derived by the phase scanning. Imaging at pupil plane 131 thus provides angular spectroscopy measurements that provide angular information and information relating to the diffraction orders, which enable a de-correlation of topographical and optical characters of target 90. Fourier transforming each pixel of pupil detector 130 through its phase values thus retrieves the spectral response per angle. Respective through-phase pupil images enable carrying out angular scatterometry procedures which enhance the information obtained from field plane imaging. In certain embodiments, specific spectral bands for illumination may be selected for each layer according to the reflectivities at each pixel which may be derived from the pixel spectrograms. Variations of spectrograms between pixels that belong to same layer may be used as a measure for topographic phase and its variability across target 90 and/or wafer 80, which allows correcting overlay errors and characterizing of process variability on a nm scale. The topographic phase per pixel may also provide additional information on the alignment of target elements having small pitches and on the from factor of segments having unresolved pitches.

For example, the angular spectral signature may enable measuring and monitoring thickness and optical parameters of deposited films and layers of target 90. Furthermore, as phase scanning is sensitive to the refractive index of the film, phase scanning enables measurement of the exposed resist latent image, namely the measurement of the exposed resist quality before resist development. This option is facilitated by the refractive index change in the exposed areas relative to the unexposed areas of the wafer.

In certain embodiments, method 200 comprises measuring of the exposed layer quality before layer development using a refractive index sensitivity of the interferometry images with respect to the phase differences, using the phase scanning (stage 294). In certain embodiments, method 200 comprises monitoring resist latent image from the interferometry images (stage 295) and reconstructing film structure and refractive properties (stage 296). Imaging unit 152 may be arranged to generate interferometry images 170 at pupil plane 131 and analysis unit 160 may be arranged to characterize target 90 from angular information obtained at pupil plane 131.

In certain embodiments, imaging unit 130 may be arranged to generate corresponding interferometry images at both pupil and field planes (i.e., comprise both pupil detector 130 and field detector 140), and analysis unit 160 may be arranged to derive and relate angular and spectroscopic information from the respective plane. In such embodiments, imaging unit 152 may comprise beam splitter 135 arranged split interferometry images 170 between pupil camera 130 and field camera 140.

In certain embodiments, method 200 comprises generating the interferometry images in both pupil and field planes simultaneously (stage 225), deriving layer quality measurements from the grabbed interferometry images (stage 290) and deriving and monitoring thickness and optical parameters of deposited films as the target characteristics (stage 292).

Improved Focusing by Phase Adjustment

In certain embodiments, system 100 may be further arranged to refine focusing by introducing a phase difference derived from the interferometry images, and method 200 may further comprise refining focus signal calculation by adapting the phase (stage 300), e.g., by adding a reference phase to the through focus collected images when deriving the contrast function (stage 302) and optimizing the required phase difference for best contrast function in a training stage (stage 304). In certain embodiments, the focusing may be refined by adjusting the illumination phase with respect to an anchored focus position, wherein the adjustment may be calculated from through focus images with respect to the resulting image contrast. Additionally, the contrast function quality may be improved by introducing phase adjustments.

Providing Metrology Measurements

In certain embodiments, method 200 comprises generating metrology measurements (e.g., overlay metrology) from the grabbed interferometry images (stage 280). In particular, combining angular and spectroscopic scatterometry techniques increases the overall data available for the overlay measurement.

Advantageously, in certain embodiments, method 200 and system 100 enable monitoring SWA with existing imaging overlay tools by adding the phase scanning elements. Furthermore, in certain embodiments, method 200 and system 100 enable monitoring film thickness and optical parameters as well as monitoring latent images (e.g., of resist or other layers) with existing imaging overlay tools. In certain embodiments, method 200 and system 100 enable combining the three metrology technologies of imaging, angular scatterometry and spectroscopic scatterometry into a single tool.

In certain embodiments, method 200 comprises controlling input and output polarization to refine the measurements and analysis (stage 320). Such control may be used to enhance any of the above mentioned applications In certain embodiments, method 200 comprises applying a training stage to characterize typical target asymmetries (stage 330) and identifying the characterized typical target asymmetries during runs (stage 335).

Advantageously, the phase characterization can distinguish reflections from different layers, a feature which allows more accurate spectral characterization of target features than spectral measurements without phase manipulation. In comparison to SEM (scanning electron microscopy) and scatterometry methods, phase characterization of targets is significantly less computationally extensive, less dependent on modeling, faster and yield better results in certain types of target characteristics due to removal of correlations between spatial and angular data. In particular, grabbing interferometry images in both pupil and field planes unifies functions which previously required separate instruments. Additionally, the use of phase controlled interferometry allows better focusing in target with low contrast.

In the above description, an embodiment is an example or implementation of the invention. The various appearances of "one embodiment", "an embodiment", "certain embodiments" or "some embodiments" do not necessarily all refer to the same embodiments.

Although various features of the invention may be described in the context of a single embodiment, the features may also be provided separately or in any suitable combination. Conversely, although the invention may be described herein in the context of separate embodiments for clarity, the invention may also be implemented in a single embodiment.

Certain embodiments of the invention may include features from different embodiments disclosed above, and certain embodiments may incorporate elements from other embodiments disclosed above. The disclosure of elements of the invention in the context of a specific embodiment is not to be taken as limiting their used in the specific embodiment alone.

Furthermore, it is to be understood that the invention can be carried out or practiced in various ways and that the invention can be implemented in certain embodiments other than the ones outlined in the description above.

The invention is not limited to those diagrams or to the corresponding descriptions. For example, flow need not move through each illustrated box or state, or in exactly the same order as illustrated and described.

Meanings of technical and scientific terms used herein are to be commonly understood as by one of ordinary skill in the art to which the invention belongs, unless otherwise defined.

While the invention has been described with respect to a limited number of embodiments, these should not be construed as limitations on the scope of the invention, but rather as exemplifications of some of the preferred embodiments. Other possible variations, modifications, and applications are also within the scope of the invention. Accordingly, the scope of the invention should not be limited by what has thus far been described, but by the appended claims and their legal equivalents.

What is claimed is:

1. A system comprising:
   an illumination source arranged to produce electromagnetic radiation having a coherence length of less than 30 microns;
   a reference optical element;
   a phase controlled interferometer arranged to:
   receive the radiation from the illumination source;
   split the radiation between a target and the reference optical element, wherein the interferometer is arranged to controllably introduce a phase between radiation directed to the target and to the reference optical element; and,
   generate, from reflected radiation from the target and from the reference optical element, an interference beam;
   an imaging unit arranged to receive the interference beam and generate a plurality of interferometry images derived using phase characterization corresponding to different introduced phases at at least one of a pupil plane and a field plane, wherein the plurality of interferometry images are used to introduce a phase difference with the phase controlled interferometer to refine a focus signal calculation.

2. The system of claim 1, wherein the illumination source is arranged to produce radiation having at least one band within a wavelength range of 170-900 micron.

3. The system of claim 1, wherein the reference optical element comprises a reference objective which is identical to a target objective and a mirror.

4. The system of claim 1, wherein the reference optical element comprises a mirror.

5. The system of claim 1, wherein the phase controlled interferometer comprises a beam splitter which is mechanically adjustable to control the introduced phase.

6. The system of claim 5, wherein the phase controlled interferometer is arranged to scan the phase through the coherence length of the radiation.

7. The system of claim 1, wherein the imaging unit is arranged to generate the interferometry images at the pupil plane.

8. The system of claim 1, wherein the imaging unit is arranged to generate the interferometry images at the field plane.

9. The system of claim 1, wherein the imaging unit is arranged to generate corresponding interferometry images at both pupil and field planes.

10. The system of claim 1, wherein the imaging unit comprises a beam splitter arranged split the interferometry images between a pupil camera and a field camera.

11. The system of claim 1, wherein the at least one target characteristic comprises at least one of: target topography, target side wall angles (SWA), a target asymmetry merit, film thickness, film optical parameters and exposed layer quality before layer development.

12. The system of claim 1, wherein the phase controlled interferometer is further arranged to refine focusing by introducing a phase difference derived from the interferometry images.

* * * * *